United States Patent

Nelson et al.

[11] Patent Number: 5,981,828
[45] Date of Patent: Nov. 9, 1999

[54] COMPOSITE ALLOGRAFT, PRESS, AND METHODS

[75] Inventors: Carl Nelson, Little Rock, Ark.; J. Marcus Hollis, Milton, Fla.; Charlene Flahiff, North Little Rock, Ark.; William Hogue, Little Rock, Ark.

[73] Assignee: Board of Trustees of the University of Arkansas, Little Rock, Ark.

[21] Appl. No.: 09/121,938

[22] Filed: Jul. 24, 1998

Related U.S. Application Data

[62] Division of application No. 08/647,424, Mar. 11, 1996, Pat. No. 5,824,078.

[51] Int. Cl.$^6$ .................................. A61F 2/28; A61F 2/32
[52] U.S. Cl. ................................................... 623/16; 623/22
[58] Field of Search .................................. 623/16, 17, 18, 623/22, 23, 66

[56] References Cited

U.S. PATENT DOCUMENTS

| | | | |
|---|---|---|---|
| 3,686,922 | 8/1972 | Bley | 72/441 |
| 3,741,706 | 6/1973 | Conley et al. | 425/406 |
| 3,786,676 | 1/1974 | Kovolyshun et al. | 73/94 |
| 4,678,470 | 7/1987 | Nashef et al. | 623/16 |
| 4,904,265 | 2/1990 | MacCollum et al. | 623/22 |
| 5,133,771 | 7/1992 | Duncan et al. | 623/23 |
| 5,176,711 | 1/1993 | Grimes | 623/22 |
| 5,326,368 | 7/1994 | Collazo | 623/22 |
| 5,329,846 | 7/1994 | Bonutti | 100/50 |

OTHER PUBLICATIONS

"Bone Grafting in Total Hip Replacement for Acetabular Protrusion," *J. Bone & Joint Surg.*, vol. 62–A, No. 7 (Oct. 1980).

"Bone Grafting in Total Hip Replacement for Acetabular Protrusion," *Acta Orthop. Scand.*, 55 (1984).

"Impacted Cancellous Allografts and Cement for Revision Total Hip Arthroplasty," *J. Bone & Joint Surg.*, Vo. 75–B, No. 1 (Jan. 1993).

*Primary Examiner*—David J. Isabella
*Attorney, Agent, or Firm*—Ray F. Cox, Jr.; J. Charles Dougherty

[57] ABSTRACT

A composite allograft press comprises a loading frame and a two piece mold to form an composite allograft and in particular an acetabular cup from impacted cancellous bone chips and cement. Pressure is applied by a manually operated lever through a rack-and-pinion gear mechanism to a plunger attached to one part of the mold. Compression load switches in-line with the plunger indicate the correct loading to the mold to produce a composite allograft in which the inner surface is smooth and comprised essentially of hardened bone cement material. The outer portion of the allograft may have limited cement extrusions but the exterior of the cup primarily shows exposed cancellous bone surface. In surgery a composite allograft; e.g., an acetabular cup, is fixed in the acetabulum with bone screws to fill an acetabular defect. A plastic liner is affixed with bone cement directly to the composite allograft cup to receive the femoral component.

3 Claims, 13 Drawing Sheets

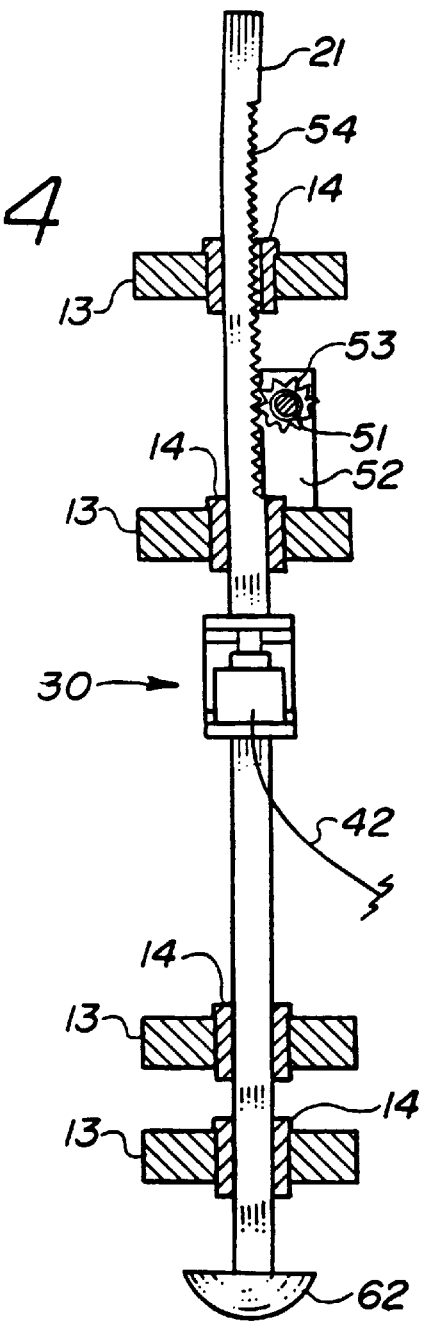
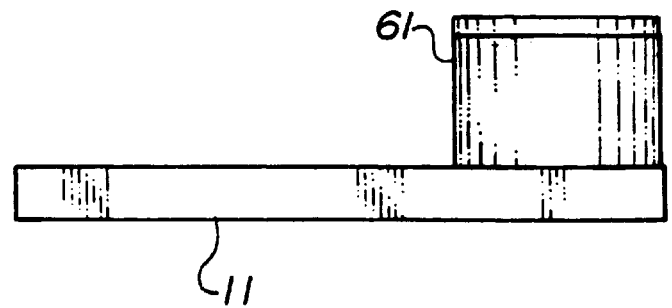
FIG. 4

COMPOSITE ALLOGRAFT, PRESS, AND METHODS

This application is a divisional application of U.S. application Ser. No. 08/647,424, filed Mar. 11, 1996, now U.S. Pat. No. 5,824,078 which is hereby incorporated by reference herein.

BACKGROUND OF THE INVENTION

The present invention relates to composite allografts used in orthopedic surgery, and in particular to a composite acetabular allograft cup, to a method and apparatus for forming the composite acetabular allograft cup, and to a method of using the composite acetabular allograft cup in hip replacement surgery.

There is a need for methods of replacing or strengthening certain types of bone defects; for example, in the case of hip replacement surgery. A hip joint is a ball and socket joint in which the ball is the femoral head and the socket is called the acetabulum (due to its supposed resemblance to a vinegar cruet). The cavity of the acetabulum is formed from three parts of the pelvic bone: above by the ilium, behind and below by the ischium, and internally by the os pubis. Patients who are otherwise candidates for hip replacement surgery may have acetabular defects. The acetabulum may for various reasons, including disease, trauma or prior surgery, contain defects such as missing or eroded portions of the acetabular wall. These defects must be corrected or compensated if the surgery is to be successful.

In hip replacement surgery, a hip joint prosthesis, comprising a femoral component and an acetabular component, is employed to replace the femoral head and the acetabulum. The acetabular component may include a hemispherical metal cup or ring and a low-friction plastic liner of ultra-high molecular weight polyethylene. The procedure may also be done without the metal cup, using only the liner which is cemented in place.

One method of dealing with an acetabular defect is to repair the defect with a bone graft (either an allograft, typically harvested from a cadaver, or an autograft from the patient's own bone tissue). Due to the significant weight bearing role of the hip joint, the stability and strength of the bone graft is a major concern. Metallic support cups may be required to support the bone graft material as disclosed in MacCollum (U.S. Pat. No. 4,904,265). MacCollum discloses a support cup in the shape of a rigid metallic hemisphere with a flange to support the bone graft. The outer surface of the support cup is disclosed to be porous to support bone ingrowth. A bearing insert of low friction material for receiving the ball of the femoral prosthesis is mounted within the support cup.

As an alternative to bone grafts, Grimes (U.S. Pat. No. 5,176,711) discloses an acetabular hip prosthesis in which the acetabular component of the prosthesis includes an augmentation piece to fill a rim or cavitary defect. Likewise, Collazo (U.S. Pat. No. 5,326,368) discloses a modular prosthetic acetabular cup to provide various cross sections as desired to fill acetabular defects.

Another method of remedying an acetabular defect is disclosed in "Bone Grafting in Total Hip Replacement for Acetabular Protrusion" by McCollum, et al., *Journal of Bone and Joint Surgery*, Vol. 62-A, No. 7, 1065–1073 (October 1980). The McCollum article discloses the use of wafers of bone to fill a defect in the acetabular wall.

A slightly different technique is disclosed in "Bone Grafting in Total Hip Replacement for Acetabular Protrusion" by Slooff, et al., *Acta Orthop. Scand*, 55, 593–596, (1984). While Slooff et al. disclose the use of a bone graft to close an acetabular defect, Slooff et al. also disclose surrounding the graft with a wall of cancellous bone chips which are molded and impacted by using the socket trial prosthesis. (Cancellous bone has a spongy or lattice-like structure and may be derived from cadaverous bone tissue such as femoral heads.) Slooff et al. disclose a technique of repairing an acetabular defect in which cancellous bone chips are molded and impacted around a bone graft, but do not disclose the addition of cement to the impacted bone chips.

Gie, et al. in "Impacted Cancellous Allografts and Cement for Revision Total Hip Arthroplasty," *The Journal of Bone and Joint Surgery*, Vol. 75-B, No. 1, 14–21 (January 1973) disclose the use of impacted cancellous allografts and cement for fixation of the femoral component in total hip arthroplasty. The technique disclosed by Gie et al. involves packing allograft bone chips into the femoral canal using the trial femoral component. The chips are repeatedly impacted after which cement is introduced and pressurized to force the cement into the graft. Pressure is maintained until the cement has sufficiently solidified. While Gie et al. disclose impacting cancellous bone chips into the femoral canal after which cement is added to the impacted bone chips and pressurized to force the cement into the graft, Gie et al. do not disclose the use of this technique in relation to the acetabulum. Neither Slooff et al. nor Gie et al. disclose the formation of a composite acetabular cup outside the body of the patient prior to surgery.

It is known to form human tissue into particular shapes to create desired natural tissue grafts. For example, U.S. Pat. No. 4,678,470 issued to Nashef et al. on Jul. 7, 1987 for "Bone-Grafting Material" discloses a bone grafting material derived from allogenic or xenogenic bone which may be machined into a predetermined shape.

U.S. Pat. No. 5,329,846 issued to Bonutti on Jul. 19, 1994 for "Tissue Press and System" discloses a press for shaping or compressing a piece of tissue by the movement of two members relative to each other. Various shapes of the two movable members may be selected so as to produce tissue in the desired shape. While the Bonutti invention is primarily directed to the compression and shaping of soft tissue, portions of the disclosure suggest the shaping of bone tissue with the addition of polymeric material (column 11, lines 11–13). Bonutti does not expressly disclose the formation of an acetabular cup using cancellous bone chips and cement. Furthermore, the Bonutti press does not disclose a press of the rack-and-pinion type. While Bonutti discloses the importance of monitoring and controlling the pressure applied to the compressed tissue, it is in the context of maintaining graft tissue in a living state to improve graft viability and tissue healing. In this context Bonutti discloses the use of pressure sensors and force-limiting means such as the mechanism found on torque wrenches. FIG. 6A of Bonutti discloses such a torque limiting mechanism and a pressure gauge.

Rack-and-pinion gearing and load switches are known in the art of manual presses used by machinists and in manufacturing environments. For example, the common arbor press may operate by means of a manual lever through rack-and-pinion gearing. See, for an example in an unrelated art, U.S. Pat. No. 3,686,922. Likewise, U.S. Pat. No. 3,741,706 issued to Conley, et al. on Jun. 26, 1973 discloses a molding device for forming a shaped object (a toy) from a soft moldable material. A manually operated lever acting through a pair of rack-and-pinion gear mechanisms is used to move one part of a mold against the other half of a mold to mold a three-dimensional object. It is known to use pressure gauges, load limiting devices and the like in presses in the manufacturing environment. An example is U.S. Pat. No. 3,786,676 which discloses a compression testing machine having an in-line load cell.

SUMMARY OF THE INVENTION

The present invention includes a device (the acetabular allograft press), a method for using the press in forming a composite acetabular allograft cup from impacted cancellous bone chips and cement, the composite acetabular allograft cup itself, and the method of using the acetabular allograft cup in hip replacement surgery.

The acetabular allograft press comprises a loading frame which applies pressure to a two piece mold in the shape of the required acetabular cup. Various sizes of molds may be employed for different patient requirements. Pressure is applied by a manually operated lever through a rack-and-pinion gear mechanism to a plunger attached to one part of the mold; i.e., the plunger head. A plurality of compression load switches are located in-line with the plunger so as to indicate the correct degree of loading to the mold.

The method of using the acetabular allograft press comprises the following steps:

(a) A quantity of cancellous bone chips is placed in the mold (cancellous bone chips are commercially available);

(b) Pressure is applied to the bone chips to cause the chips to conform to the shape of the mold (it is important that the load applied to the bone chips is limited to avoid crushing the bone to more than a minor degree);

(c) The mold is opened and additional bone chips are added to fill any voids;

(d) A load is again placed on the bone chips to cause the newly added bone chips to conform to the shape of the mold;

(e) Commercially available bone cement is added to the mold;

(f) The mold is again loaded and the load is maintained for a sufficient period of time for the cement to harden.

This process produces a synthetic composite acetabular cup in which the inner surface is smooth and comprised essentially of hardened bone cement material. The outer portion of the cup may have a limited proportion of cement extrusions but the major portion of the exterior of the cup shows exposed cancellous bone surface. The acetabular cup is therefore suited to provide a smooth, strong inner surface to receive an acetabular implant, while the outer surface is suited for encouraging bone growth from the acetabulum into the exposed bone of the acetabular cup. While this technique is disclosed with reference to the particular application of an acetabular cup, the same techniques offer advantages in other applications where an allograft having the described properties is desirable. The present invention should not, therefore, be seen as limited to one particular application.

In surgery, the acetabular cup is highly advantageous since it avoids the necessity of performing grafting to correct acetabular defects such as by the method disclosed in Gie et al. The acetabular cup made by the method of the present invention could be formed in advance of surgery. During surgery the acetabular cup is positioned in the acetabulum so as to fill the acetabular defect and fixed in place by screws. The remainder of the total hip replacement surgery would be carried out using well known techniques. Using the surgical method of the present invention, however, a metal acetabular cup component is not required. A high density plastic liner is affixed with bone cement directly to the synthetic composite acetabular cup to receive the femoral component. The use of the apparatus and methods of the present invention are not limited to the acetabulum, but may be used to form synthetic allografts for other purposes in orthopedic surgery which would be apparent to one skilled in the art.

It is therefore an object of the present invention to provide for a synthetic composite allograft, a method of forming a composite allograft, and method of employing a composite allograft in surgical procedures.

It is also an object of the present invention to provide for a synthetic composite acetabular cup for the repair of acetabular defects encountered in total hip replacement surgery.

It is a further object of the present invention to provide for a synthetic composite allografts, and in particular for a synthetic composite acetabular cup, which presents a smooth, strong inner surface of hardened cement material and an outer surface consisting essentially of compacted cancellous bone chips.

It is also an object of the present invention to provide for a press and mold capable of producing a synthetic composite allograft, and in particular a composite acetabular cup, which presents a strong inner surface of hardened cement material and an outer surface consisting essentially of compacted cancellous bone chips.

It is a still further object of the present invention to provide for a method of using a press and mold to produce a synthetic composite allograft, and in particular a composite acetabular cup, which presents a strong inner surface of hardened cement material and an outer surface consisting essentially of compacted cancellous bone chips.

It is an additional object of the present invention to provide for a method of using a synthetic composite allograft in surgical procedures, and in particular a composite acetabular cup in total hip replacement surgery.

Further objects and advantages of the present invention will become apparent from an examination of the detailed description of the preferred embodiments considered in conjunction with the appended drawings as described hereinafter.

BRIEF DESCRIPTION OF THE DRAWINGS

FIG. 4 is a partial sectional side elevational view of the press and mold for producing a synthetic composite acetabular cup showing the plunger head retracted from the mold.

DETAILED DESCRIPTION OF THE PREFERRED EMBODIMENTS

Figure 1:
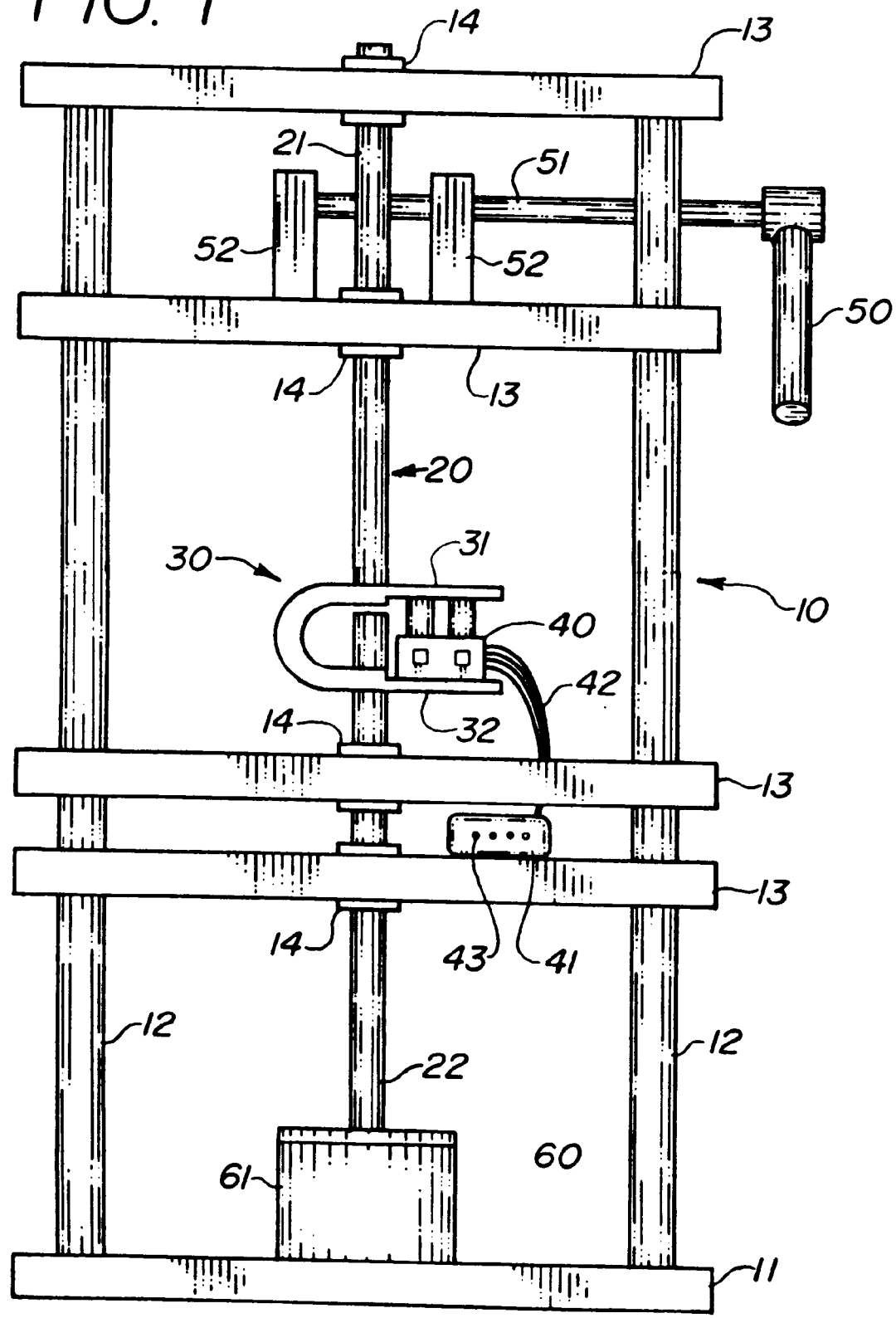
FIG. 1 is a front elevational view of the press and mold for producing a synthetic composite acetabular cup showing the plunger head depressed into the mold.

The press of the present invention may be described generally with reference to FIGS. 1 through 4. The main components of the press are mounted on a loading frame generally designated 10. The loading frame 10 comprises a base plate 11 on which is mounted a plurality of vertical support columns 12. The support columns 12 carry a plurality of transverse plates 13. Each transverse plate 13 carries a linear bearing 14 which is vertically oriented. The linear bearings 14 are aligned to accept a plunger generally designated as 20. The plunger 20 is constrained and guided by the linear bearings 14 to move up and down vertically with respect to the loading frame 10.

The plunger 20 comprises an upper component 21 and a lower component 22. At least two linear bearings 14 are disposed to guide the upper component 21 and at least two linear bearings 14 are disposed to guide the lower component 22. This arrangement assures that the plunger 20 is guided properly in linear vertical manner. Disposed between the upper component 21 and lower component 22 of the plunger 20 is a compression yoke 30. The compression yoke 30 comprises an upper arm 31 affixed to the upper component 21 of the plunger 20 and a lower arm 32 affixed to the lower component 22 of the plunger 20.

The compression yoke 30 is a precisely calibrated component which deforms in response to a compression load applied between the upper arm 31 and lower arm 32. Therefore, due to the connection between the compression yoke 30 and the upper component 21 and lower component 22 of the plunger 20, any load applied to the plunger 20 results in a precisely known and measurable deformation of the compression yoke 30. The deformation of the compression yoke 30 is reflected in a deflection of the upper arm 31 with respect to the lower arm 32.

A plurality of load switches 40 is disposed between the upper arm 31 and lower arm 32 of the compression yoke 30. Each load switch 40 is activated sequentially by increasing loads applied to, and therefore increasing deflections of, the compression yoke 30. Since a load of approximately 1000 pounds will produce unacceptable crushing of the cancellous bone chips, the load switches may advantageously be set at increments below this level; e.g., at 250, 500, 750, and 1000 pounds of force. Each load switch 40 is electrically connected to a display 41 by means of a cable 42. The load switches 40 are set in a sequence so that a gradually increasing load applied to the plunger 20 activates each load switch 40 in sequence at a particular predetermined load. The activation of a particular load switch 40 results in the illumination of an indicator light 43 on the display 41. (In the preferred embodiment of the present invention, the indicator lights 43 are light emitting diodes (LED's).) Thus, a particular desirable range of loads may be predetermined in advance so that the desirable range of loads is precisely and visually indicated by the illumination of a particular sequence of indicator lights 43. The optimum load range for the practice of the present invention is from about 250 pounds to about 500 pounds. While the particular combination of the compression yoke 30 in conjunction with a plurality of load switches 40 and indicator lights 43 has been found to be effective in the practice of the present invention, the present invention is not limited to any particular means of measuring and indicating a particular compression load. Other forms of measuring and indicating a compression load applied to the plunger 20 would be readily apparent to one skilled in the art and the present invention is intended to encompass such alternative means for measuring and indicating a compression load.

Figure 2:
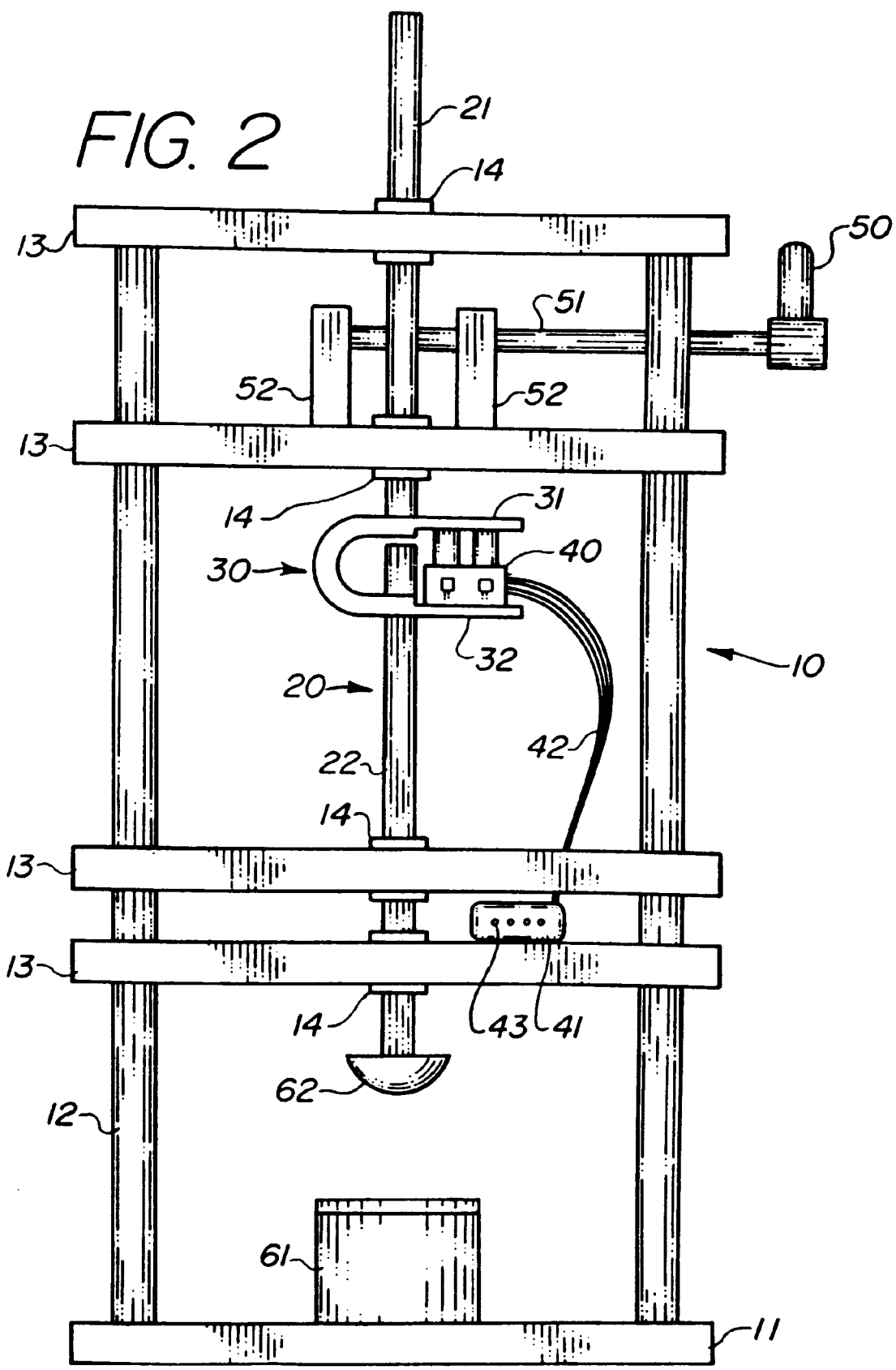
FIG. 2 is a front elevational view of the press and mold for producing a synthetic composite acetabular cup showing the plunger head retracted from the mold.
Figure 3:
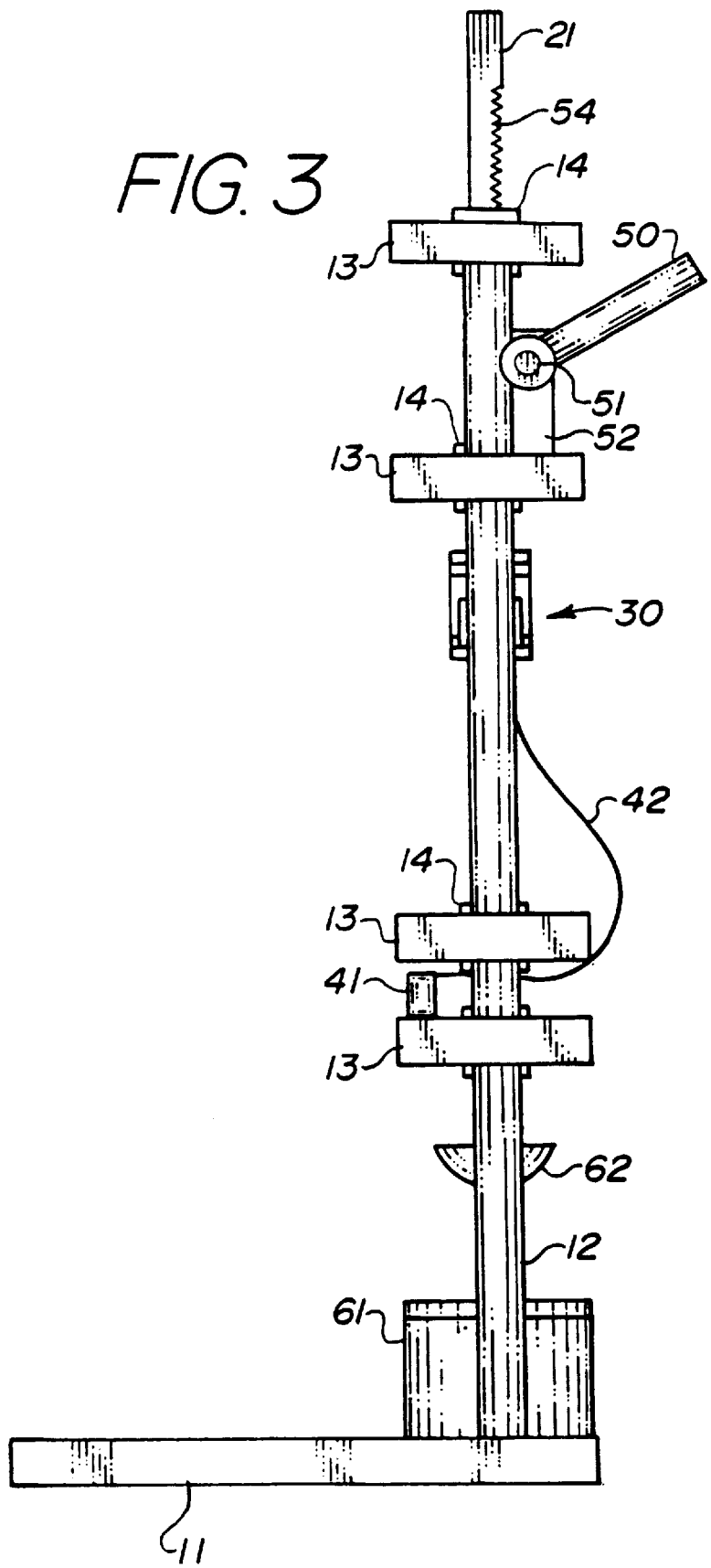
FIG. 3 is a side elevational view of the press and mold for producing a synthetic composite acetabular cup.

In the preferred embodiment of the present invention, a compression load is applied to the plunger 20 by means of a manually operated rack-and-pinion gearing system. With reference to FIGS. 1 and 2, a manually operated handle 50 is connected to a shaft 51 which is constrained to move in a rotary fashion by rotary bearings 52. Manual operation of the handle 50 results in rotary motion of the shaft 51.

With reference to FIG. 4, a pinion gear 53 affixed to the shaft 51 is operatively engaged with a rack gear 54 disposed on the upper component 21 of the plunger 20. Manual operation of the handle 50 results in rotary motion of the shaft 51 and through the rotation of the pinion gear 53 causes vertical motion of the plunger 20 by virtue of the action of the pinion gear 53 on the rack gear 54.

With reference to FIGS. 1 through 4, a two-piece mold 60 comprising an outer mold 61 which is affixed to the base plate 11 and an inner mold 62 which is affixed to the lower component 22 of the plunger 20 is employed to form a composite allograft as will be described more fully hereinafter. It should be noted that the preferred embodiment of the present invention is described with respect to a mold for forming a composite acetabular allograft cup. The present invention is not limited to this particular application nor to the particular shape described for use as an acetabular cup. Any predetermined shape which can be formed by a two piece mold is suitable for the practice of the present invention.

In the particular case of a mold 60 for forming a composite acetabular allograft cup, a series of molds having the same general shape, namely that of a hemispherical dome, but of varying sizes to accommodate the varying sizes of the acetabulum found in different human patients, is desirable. For example, a series of molds with diameters from 60 to 70 millimeters at 2 millimeter increments would be adequate for most purposes. While the drawing figures illustrate a shape having a smooth inner surface, the scope of the present invention is not so limited. A shape having ridges or some other form of textured surface may have advantages in some applications.

Figure 9:
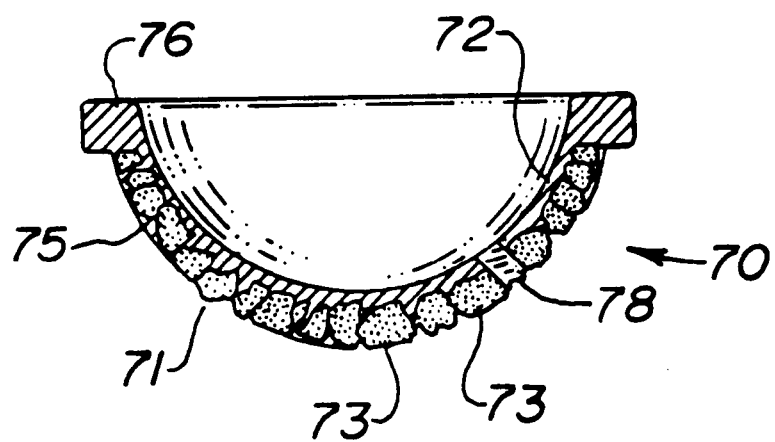
FIG. 9 is a sectional elevational view of the synthetic composite acetabular cup.

The use of the composite allograft press described above may be described with reference to FIGS. 1 through 4 and in particular to FIGS. 5 and 6. First, a mold 60 is made to a predetermined shape as appropriate for the particular allograft application. In the particular case of a composite allograft used to repair defects in the acetabular wall, an acetabular cup 70 in the shape of a hollow hemispherical dome is desirable. Accordingly, the mold 60 illustrated in FIGS. 1 through 6 comprises an outer mold 61 having a hemispherical shape appropriate to the outer surface 71 of the acetabular cup 70 and an inner mold 62, likewise having a similar hemispherical shape although of a smaller radius, so that the combination produces a hollow hemispherical dome sized to fit within the patient's acetabulum. The hollow hemispherical dome of the composite acetabular allograft cup 70 further has an inner surface 72 as shown in FIG. 9 sized to receive the other components required in total hip replacement as will be described more fully hereinafter.

In order to form a composite allograft, a quantity of cancellous bone chips 73 is placed in the outer mold 61. Cancellous bone chips are derived from cadaverous bone and are characterized by a spongy or lattice-like structure. The cancellous bone chips 73 have the property of encouraging and accepting bone ingrowth from the defective acetabulum. Cancellous bone chips are commercially available. A size of one cubic centimeter is optimum for the practice of the invention, although a range of sizes above and below the optimum would be acceptable.

After placing the cancellous bone chips 73 in the outer mold 61, a load is applied manually via the handle 50 to the plunger 20 and thereby to the inner mold 62. The load applied to the cancellous bone chips 73 is for the purpose of conforming the cancellous bone chips 73 to the shape of the outer mold 61. A minor amount of crushing of the cancellous bone chips 73 is acceptable and may even be desirable to assist in forming a compact and somewhat consolidated mass. However, excessive crushing of the bone chips could lead to the closing off of the lattice-like structure of the cancellous bone chips 73 so as to interfere with the desirable ingrowth of bone from the acetabulum once the acetabular cup 70 is implanted. Therefore, the operator may rely on the indicator lights 43 to avoid the application of excessive loads to the mold 60. As noted above, the optimum range of loads is from about 250 to about 500 pounds. Loads of 1000 pounds or above should be avoided.

After conforming and consolidating the cancellous bone chips 73, the mold 60 is opened and the consolidated cancellous bone chips 73 inspected for voids. If any voids occur, additional cancellous bone chips 73 may be added to the mold 60. A load is then reapplied to the mold 60 to consolidate the newly added cancellous bone chips 73. This process may be repeated as often as necessary to fill and consolidate any voids in the mass of cancellous bone chips 73.

Once the cancellous bone chips 73 have been consolidated and conformed to the outer mold 61 so as to form the desired outer surface 71 without significant voids, a quantity of commercially available bone cement 74 is added to the mold 60. The bone cement will typically be a methyl methacrylate type. A load is then reapplied to the mold 60 so as to cause the newly added bone cement 74 to conform to the inner mold 62 so as to form the desired inner surface 72 of the acetabular cup 70. The load is maintained on the mold 60 for a sufficient period of time for the bone cement 74 to harden. The amount of time required for the bone cement 74 to harden depends on the particular type of cement used and other environmental conditions. For commercially available methyl methacrylate bone cement, the setting time will be approximately eight minutes.

The action of the inner mold 62 against the bone cement 74 causes the bone cement 74 to flow around the inner mold 62 so as to form a surface 72 conforming to the shape of the inner mold 62 and consisting essentially of hardened bone cement 74. The surface 72 is thus a smooth, uniform hardened surface of bone cement 74. However, due to the partially consolidated nature of the cancellous bone chips 73, the bone cement 74 only penetrates the partially consolidated mass of cancellous bone chips 73 to a limited extent. While limited extrusions 75 of hardened bone cement may appear on the outer surface 71, the outer surface 71 will consist essentially of the exposed surface of cancellous bone chips 73. The outer surface 71 is thus of the appropriate shape to be received in the acetabulum of the patient and further presents a surface of exposed cancellous bone chips 73 which is conducive to bone ingrowth from the acetabulum into the composite acetabular allograft cup 70.

Figure 5:
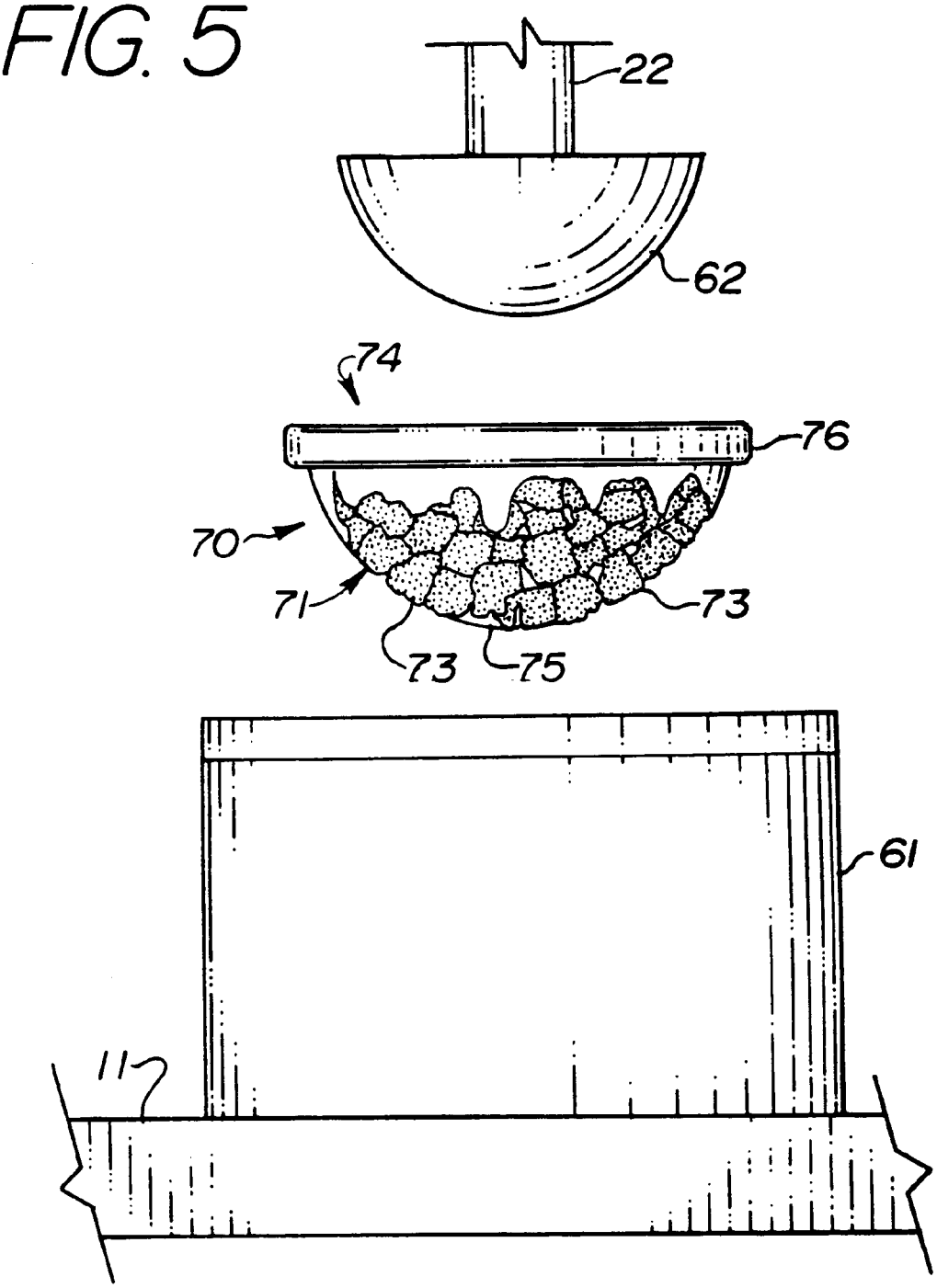
FIG. 5 is a partial exploded view of the mold, plunger head, and synthetic composite acetabular cup.
Figure 6:
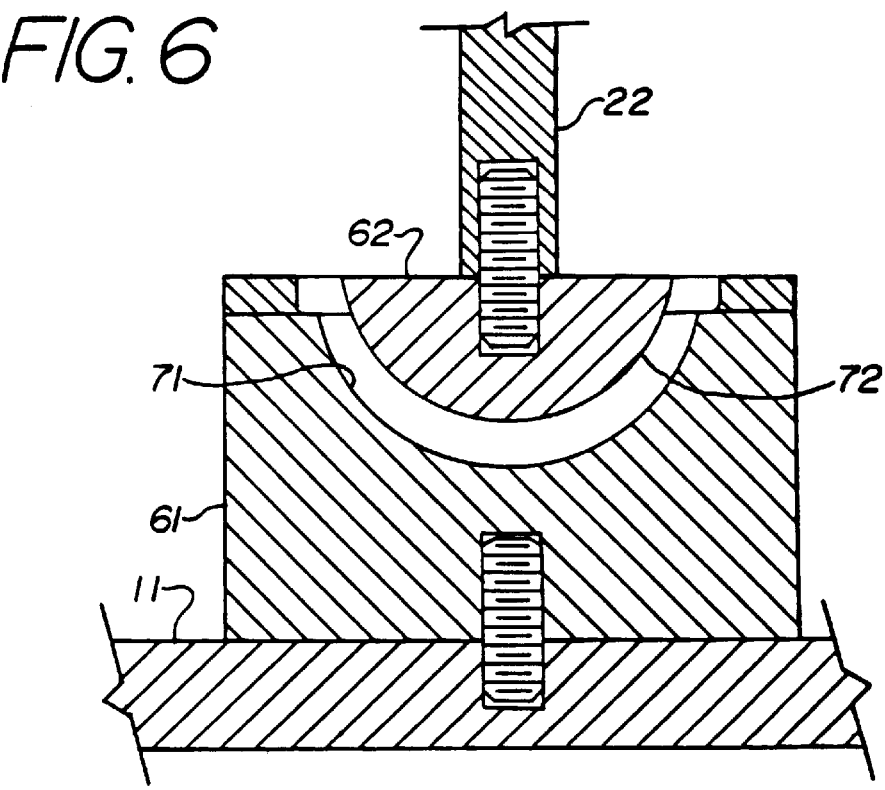
FIG. 6 is a partial sectional view of the plunger head and mold as positioned for the formation of the synthetic composite acetabular cup.
Figure 7:
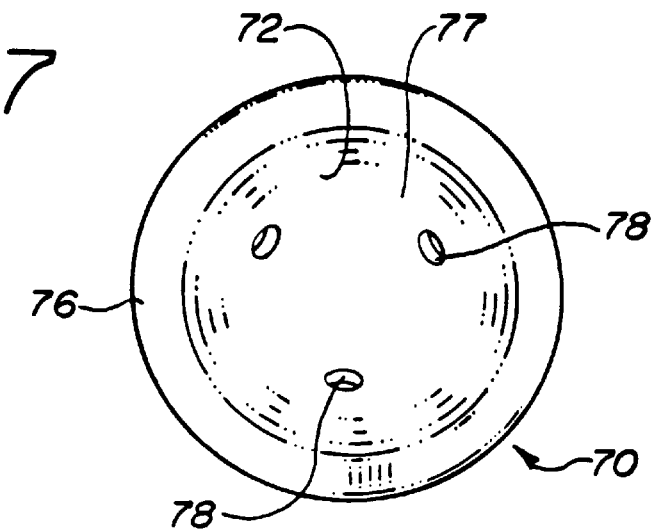
FIG. 7 is a plan view of the inner surface of the synthetic composite acetabular cup showing holes in the dome of the cup for receiving bone fixation screws.
Figure 8:
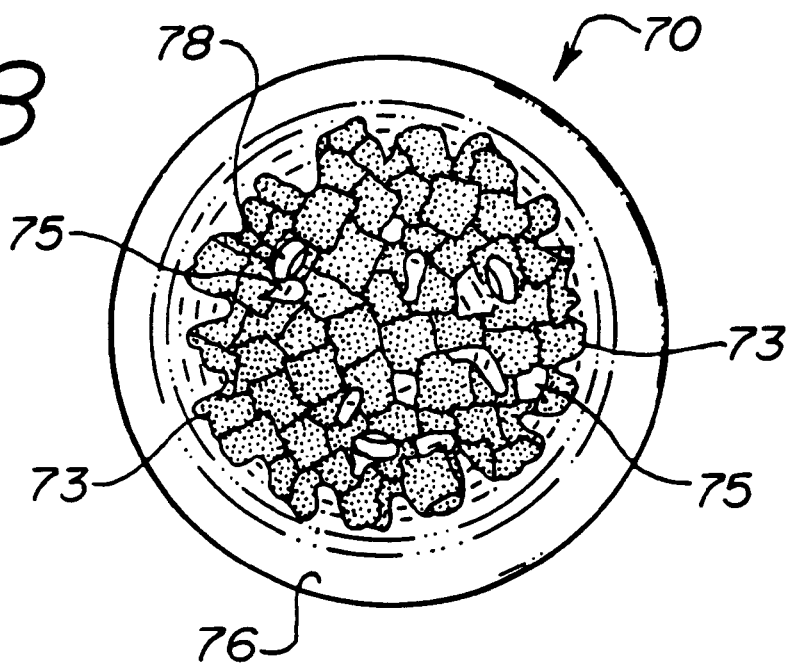
FIG. 8 is a plan view of the outer surface of the synthetic composite acetabular cup showing minimal cement extrusions amid the compacted cancellous bone chips.

While the shape of the acetabular cup 70 is essentially that of a hollow hemispherical dome, it may be noted from FIGS. 5 and 6 that a rim 76 may easily be formed in the acetabular cup 70. Such a rim 76 may be desirable in certain applications and in other applications the rim 76 is not required.

The composite acetabular allograft cup 70 formed by the method of the present invention therefore comprises a hollow hemispherical dome 77 which may be surrounded by a rim 76, as may be seen with reference to FIGS. 5, 7, 8 and 9. The composite acetabular allograft cup 70 presents an outer surface 71 comprised essentially of exposed cancellous bone chips 73 with minimal extrusions 75 of hardened bone cement 74 and an inner surface 72 comprised essentially of hardened bone cement 74. For implantation of the composite acetabular allograft cup 70, holes 78 may be drilled through the dome 77. In some applications the holes 78 may be located in the rim 76.

Figure 10:
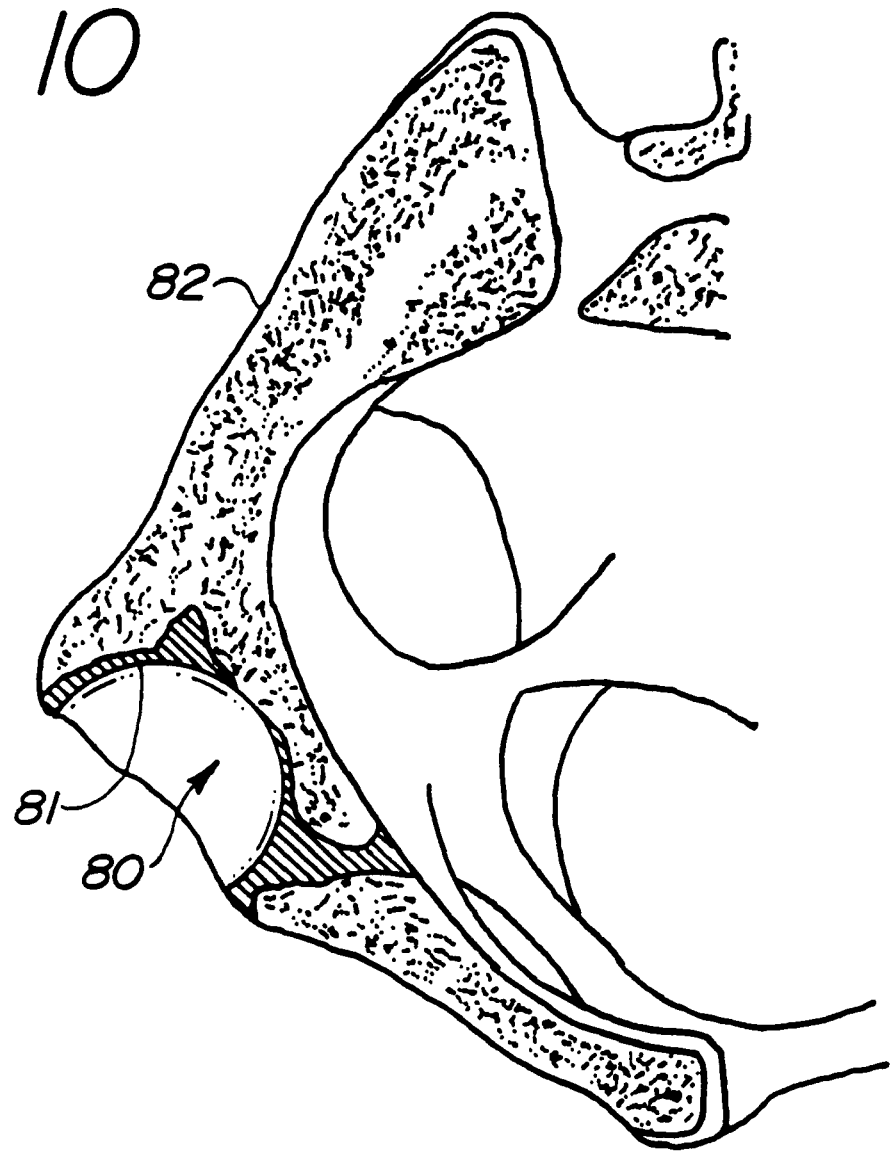
FIG. 10 is a lateral sectional view through the acetabulum showing typical defects of the acetabular wall.

The use of the composite acetabular allograft cup 70 of the present invention may be described with reference to FIGS. 10 through 15. FIG. 10 shows a lateral cross section of the acetabulum 80 showing defects 81 in the acetabular wall. The defects 81 in the acetabular wall may include eroded portions of the wall, eroded or missing portions of the rim of the acetabulum 80, and penetrations through the pelvic bone 82.

Figure 11:
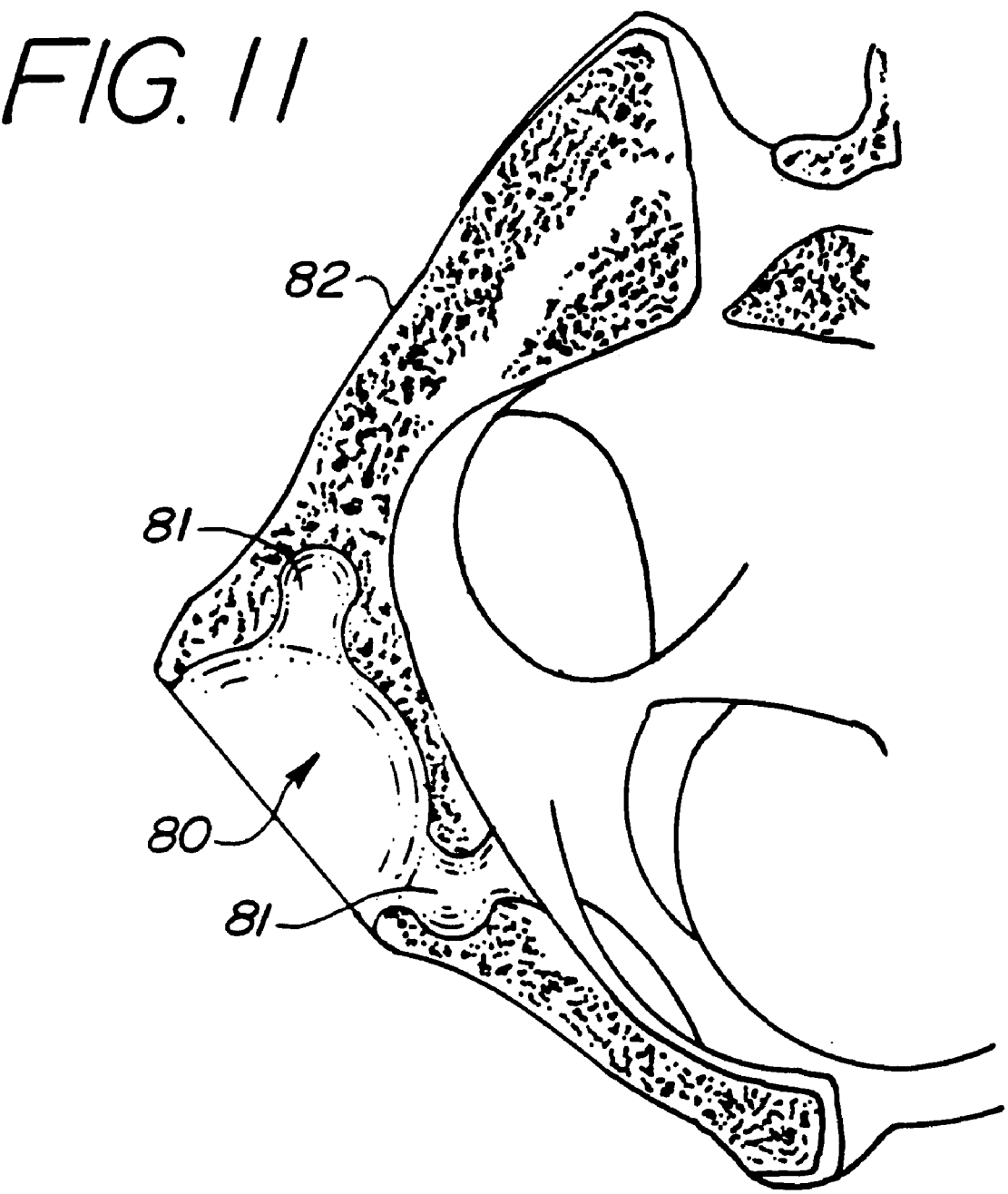
FIG. 11 is a lateral sectional view through the acetabulum showing the acetabulum prepared to receive the synthetic composite acetabular cup.
Figure 12:
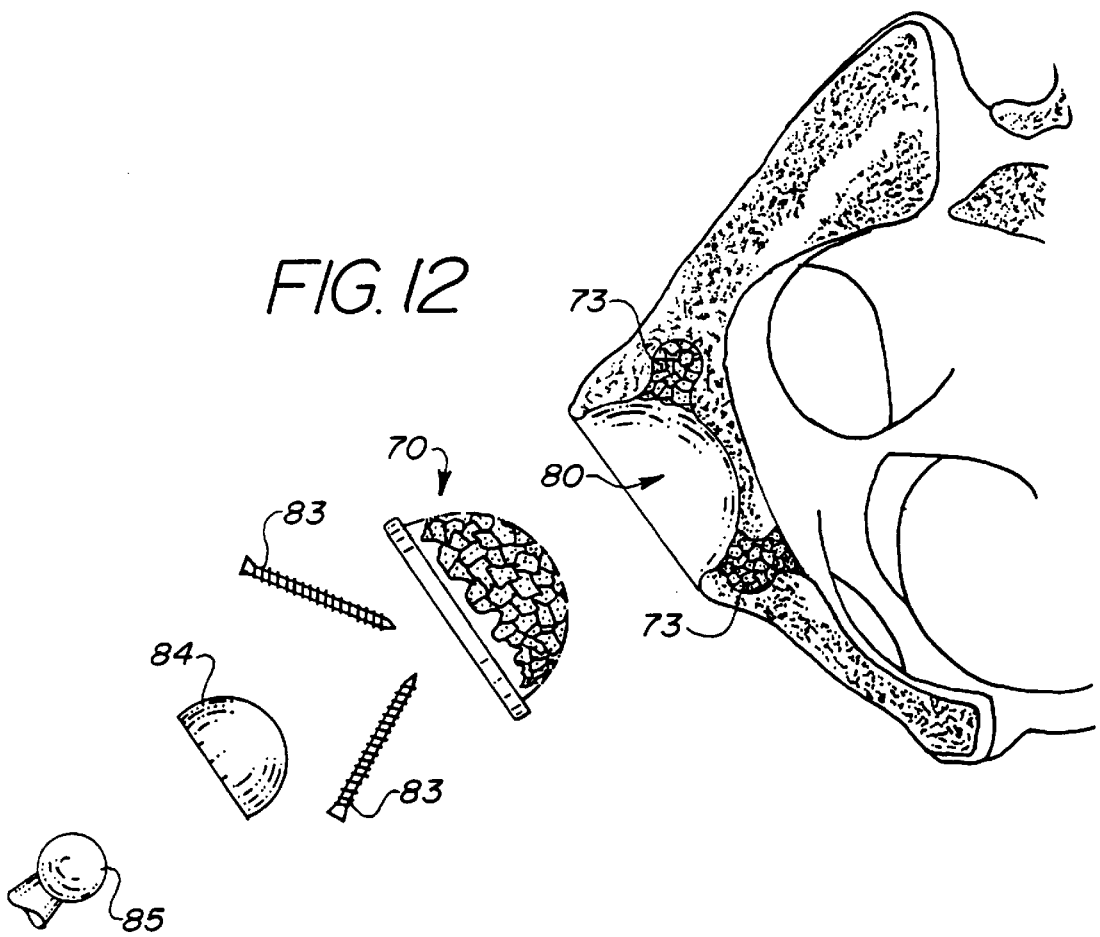
FIG. 12 is an exploded view of the components employed to implant the synthetic composite acetabular cup in relation to the sectioned acetabulum.

FIG. 11 illustrates the same lateral cross section of the acetabulum 80 showing the acetabulum 80 prepared to receive the composite acetabular cup 70 by the removal of damaged portions of the acetabular wall. Deep defects 81 in the acetabular wall may be filled with cancellous bone chips 73 as shown in FIG. 12.

The composite acetabular allograft cup 70 is employed in total hip replacement surgery generally in the following manner:

1. Holes 78 are drilled in the composite acetabular allograft cup 70 and the cup 70 is fixed in the acetabulum 80 with bone screws 83.

2. In conventional implantation of the prosthetic hip joint, a metal cup is fixed in the acetabulum 80 This is not required in the surgical method of the present invention. Instead only the high density plastic liner 84 of the acetabular component is used. The plastic liner 84 is affixed to the composite acetabular allograft cup 70 with conventional bone cement.

3. The placement of the femoral component and the remainder of the surgery is conventional.

The sequences involved in the use of the acetabular cup 70 in total hip replacement surgery may be explained more fully with reference to FIGS. 10–15 as follows: (1) the acetabulum 80 is exposed, (2) the acetabulum is reamed, (3) the acetabular cup 70 is tested for fit in the acetabulum 80, (4) the acetabular cup 70 is marked for drilling holes 78 for bone screws 83, (5) the holes 78 are drilled in the acetabular cup 70, (6) the acetabular cup 70 is affixed in place in the acetabulum 80 with bone screws 83, (7) the high density plastic liner 84 is tested for fit in the acetabular cup 70, (8) the femoral component is tested for fit in the plastic liner 84, (9) a quantity of bone cement is placed in the acetabular cup 70, and (10) the plastic liner 84 is pressed into the bone cement using an inserter.

Figure 13:
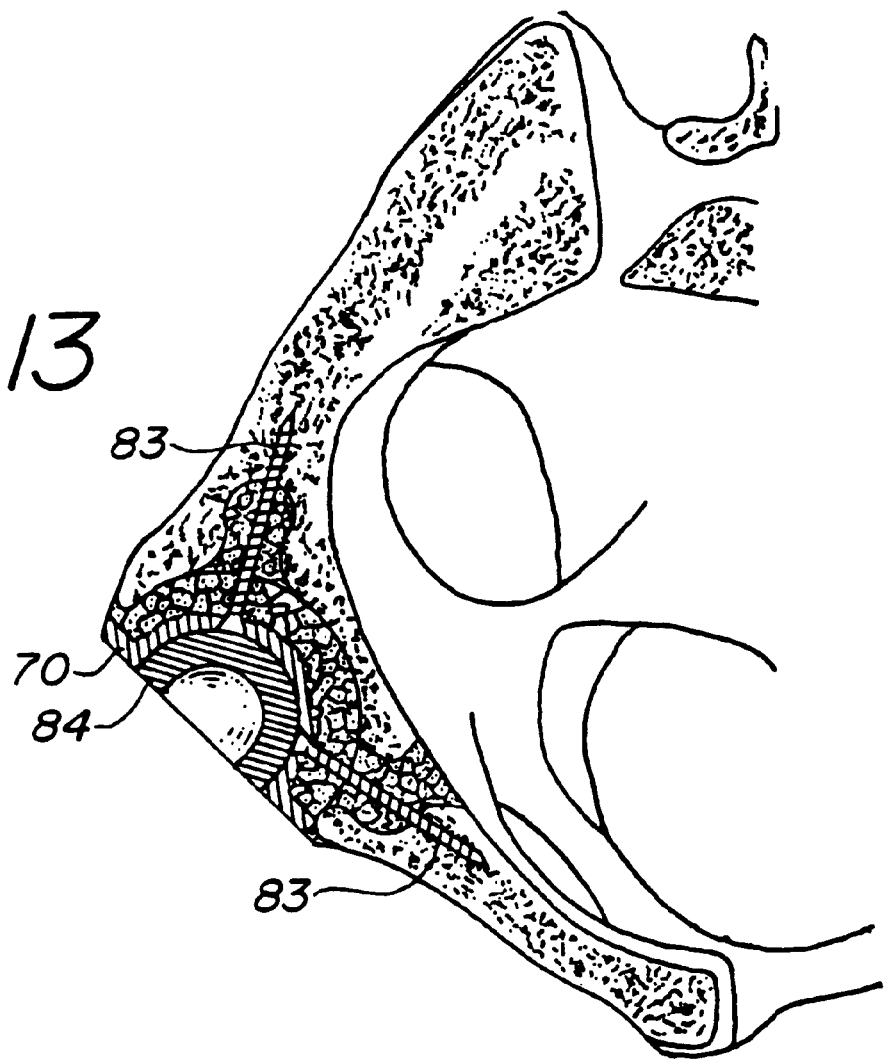
FIG. 13 is a lateral sectional view through the acetabulum with the synthetic composite acetabular cup and high density polyethylene insert implanted in the acetabulum.
Figure 14:
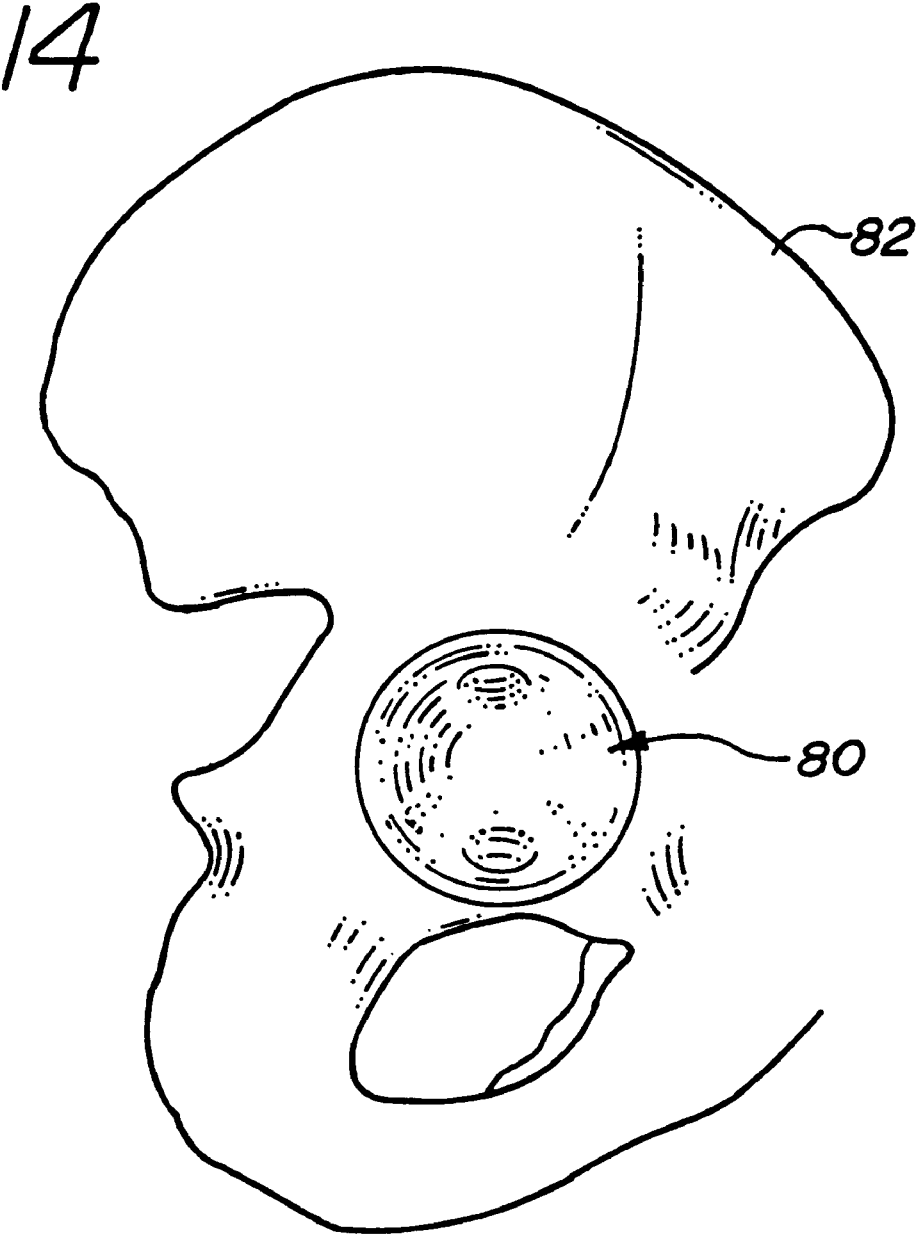
FIG. 14 is an anterior-posterior view of the acetabulum.
Figure 15:
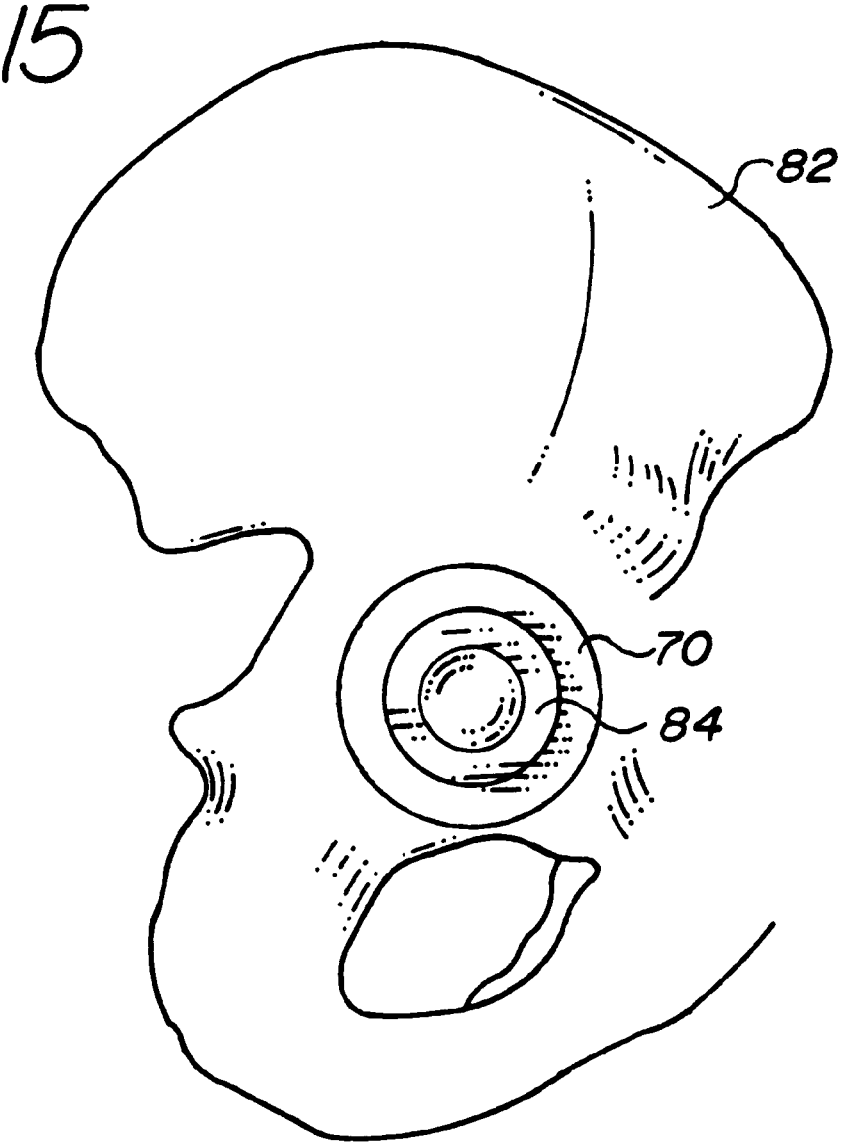
FIG. 15 is an anterior-posterior view of the acetabulum with the synthetic composite acetabular cup and high density polyethylene insert implanted in the acetabulum.

FIG. 13 shows a lateral cross-section through the acetabulum 80 with the acetabular cup 70 fixed in the acetabulum 80 and the plastic liner 84 affixed in the acetabular cup 70 with bone cement. The remainder of the procedure is conventional.

The present invention has been described with reference to certain preferred and alternative embodiments which are intended to be exemplary only and not limiting to the full scope of the present invention as set forth in the appended claims.

What is claimed is:

1. A composite allograft, comprising:

cancellous bone chips molded and compressed with bone cement to a predetermined shape having an inner surface and an outer surface;

said inner surface consisting essentially of hardened bone cement and said outer surface consisting essentially of exposed cancellous bone chips.

2. The composite allograft of claim 1 adapted for use in total hip replacement in a human patient having an acetabulum having defects in the acetabulum, wherein said predetermined shape conforms substantially to the acetabulum.

3. The composite allograft of claim 2 wherein said predetermined shape is substantially hemispherical.

* * * * *